United States Patent [19]

Marsden et al.

[11] 4,226,994
[45] Oct. 7, 1980

[54] PROCESS FOR MAKING 4-METHYL-4,5-DIHYDROTETRAZOLO [1,5-a] QUINAZOLIN-5-ONE

[75] Inventors: John H. Marsden; Norman Harrison, both of Blackley, England

[73] Assignee: Imperial Chemical Industries Limited, London, England

[21] Appl. No.: 49,902

[22] Filed: Jun. 19, 1979

[30] Foreign Application Priority Data

Jul. 4, 1978 [GB] United Kingdom ............... 28713/78

[51] Int. Cl.³ .......................................... C07D 455/00
[52] U.S. Cl. ...................... 544/251; 544/287
[58] Field of Search ................................ 544/251, 287

[56] References Cited

U.S. PATENT DOCUMENTS 4,087,422  5/1978  Bowie et al. ..................... 544/251

Primary Examiner—Paul M. Coughlan, Jr.
Attorney, Agent, or Firm—Cushman, Darby & Cushman

[57] ABSTRACT

In a process for preparing the compound 4-methyl-4,5-dihydrotetrazolo [1,5-a] quinazolin-5-one having the structural formula:

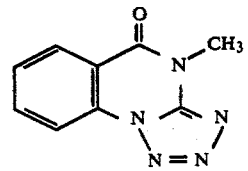

which comprises the steps of (i) bringing anthranilic acid into reaction with cyanamide at a temperature in the range of 80° to 100° C.; (ii) bringing the reaction product obtained by the foregoing step (i) into reaction with hydrazine hydrate in the presence of an organic solvent; then (iii) diazotizing the hydrazino compound so formed to yield a tetrazole; and finally (iv) methylating the tetrazole, the improvement which comprises using n-butanol as the organic solvent in step (ii).

9 Claims, No Drawings

PROCESS FOR MAKING 4-METHYL-4,5-DIHYDROTETRAZOLO [1,5-a] QUINAZOLIN-5-ONE

This invention relates to a process for preparing tetrazolo[1,5-a]quinazoline derivatives, and more particularly to an improved process for preparing the compound 4-methyl-4,5-dihydrotetrazolo[1,5-a]quinazolin-5-one, of formula:

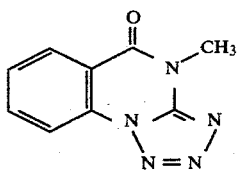

The foregoing compound is an active fungicide which is of value in combating a number of fungal diseases, in particular the disease *Piricularia oryzae* known as rice blast.

The compound, methods for preparing it, and antifungal processes and compositions using, and containing, it are described in German Offenlegungschrift No. 2539396.

An improved process for preparing the product which gives improved yields more readily, conveniently and cheaply, has been described in U.S. patent application Ser. No. 829,504, filed Aug. 31, 1977, now abandoned, which comprises the steps of brining anthranilic acid into reaction with cyanamide at an elevated temperature (Stage I); bringing the reaction product obtained by the foregoing step into reaction with hydrazine hydrate (Stage II) and then diazotising the hydrazino compound so formed to yield a tetrazole (Stage III); and finally methylating the tetrazole (Stage IV).

In the second step (Stage II) of the reaction 2-amino-quinazolin-4-one is brought into reaction with, preferably an excess of, hydrazine hydrate. The temperatures used in this second step may vary within fairly wide limits, for example between 30° C. and 200° C. In either case the reaction is preferably carried out in the presence of an organic liquid, which, in the case of the higher temperature reaction, may be, for example, ethylene glycol, or in the case of the lower temperature reaction, may be, for example, ethanol or n-propanol. In all cases an amount of an acid, such as hydrochloric acid, may be present with advantage.

According to the present invention there is provided a process for preparing the compound 4-methyl-4,5-dihydrotetrazolo[1,5-a]quinazolin-5-one having the structural formula:

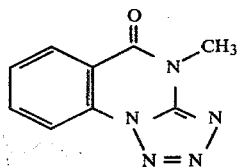

which comprises the steps of bringing anthranilic acid into reaction with cyanamide at an elevated temperature; bringing the reaction product obtained by the foregoing step into reaction with hydrazine hydrate in the presence of n-butanol and then diazotising the hydrazino compound so formed to yield a tetrazole; and finally methylating the tetrazole.

In the first step of the reaction the anthranilic acid used is preferably as pure as is commercially practicable. An aqueous paste or aqueous slurry or aqueous suspension of the acid may be employed. A suitable temperature for conducting the reaction is between 80° and 100° C., preferably between 90° and 95° C. When the reaction has been completed the pH of the reaction mixture may be adjusted to be slightly alkaline, but preferably the reaction product is filtered off, washed, and used as such, without further treatment, in the next stage, or step of the process. This is advantageous with respect to the first step of the process of U.S. patent application Ser. No. 829,504, referred to above, in that the omission of the hydrochloric acid treatment of the product, and the subsequent neutralisation, surprisingly results in the obtention of a product of much greater purity. From 1.5 to 3.5 moles, preferably 2.5 moles, of cyanamide per mole of anthranilic acid may be used.

The reaction product from this first step, is 2-amino-quinazolin-4-one having the chemical structure:

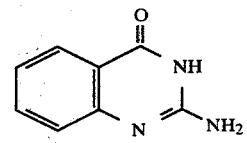

and it may, if desired, be dried, before being deployed in the second step of the reaction. Displacement washing techniques or normal drying procedures may be used, for example, to dry the product.

In the second step of the reaction the foregoing 2-amino-quinazolin-4-one is brought into reaction with hydrazine hydrate. The temperatures used in this second step may vary, for example, between 90° C. and 120° C. The reaction is carried out in the presence of n-butanol.

The advantages of this solvent are:
(1) A shorter reaction time
(2) A 50% reduction in the hydrazine usage
(3) The use a weaker hydrazine hydrate solution
(4) The use of 2-amino-quinazolin-4-one as water-wet paste.

After completion of the reaction dilution, cooling, filtration, and washing with water and drying of the product may be carried out. The product is a mixture of:

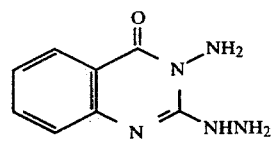

3-amino-2-hydrazino-quinazolin-4-one
and:

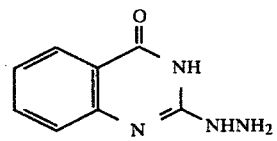

2-hydrazino-quinazolin-4-one containing mostly the latter.

Diazotisation of the mixture of products above, is preferably carried out in usual fashion, by suspending the product in dilute hydrochloric acid and adding aqueous sodium nitrite slowly to the stirred suspension below about 25° C. This higher temperature in comparison with the temperature of 8° to 10° C. deployed in diazotisation Stage III of the process of U.S. patent application Ser. No. 829,504 is advantageous in that it avoids cooling down and subsequent warming-up, saving time and energy. The compound thereby obtained is the tetrazole having the structure:

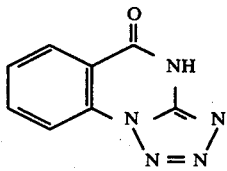

and this may be filtered off, washed with water and dried.

In the final reaction step of the invention process the above tetrazole is methylated, for example, by first suspending or dissolving it in potassium or sodium carbonate solution and then bringing it into reaction with dimethyl sulphate, preferably between 40° and 45° C. Alternatively sodium hydroxide solution may be used in which case preferably part of it is added concurrently with the dimethyl sulphate. Upon completion of the reaction the mixture may, if necessary, be warmed to about 95° C. to destroy any excess of dimethyl sulphate. It may then be cooled, or allowed to cool, and the product, having the structure:

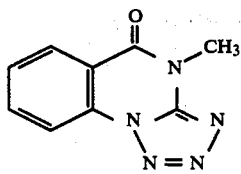

may be removed by filtration and then washed with water and dried.

As an alternative procedure, the diazotisation reaction mixture may be adjusted to pH 9, by adding caustic soda solution to it, and is then methylated with dimethyl sulphate. The addition of further alkali is necessary and this may be accomplished either by adding a metal carbonate before methylation, or by adding sodium hydroxide solution concurrently with the alkylating agent.

The invention is illustrated by the following Examples, in which the various steps in the invention process are described, by way of example only, in illustrative detail. Reference back from the examples should be made to the schematic reaction outline presented below with the starting, intermediate, and final, substances identified with numerals I, II, IIIa, IIIb, and IV; and V, respectively.

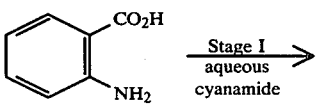

I

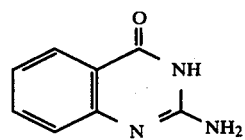

II

Hydrazine Hydrate/n-butanol 95°–120° C. | Stage II

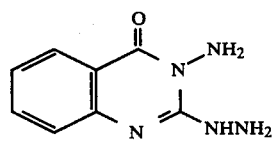

Some IIIa present which diazotises to IV

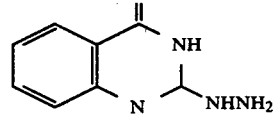

IIIb

NaNO₂/aq HCl

Stage III Diazotisation

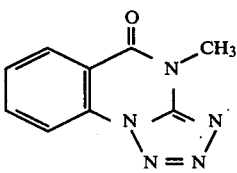

V

Stage IV DMS aqueous Na₂CO₃ or aqueous NaOH

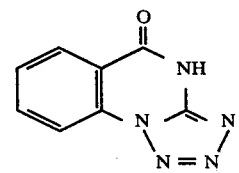

IV

The invention includes improved Stages I, II and III, of the above reaction scheme, individually, and all stages in combination.

EXAMPLE 1

The Preparation of 2-Amino-quinazolin-4-one (II)

Method I

Dry anthranilic acid (27.9 g @ 98.2%=27.4 g @ 100%; 0.2 mole), aqueous cyanamide liquor (42 g @ 50%=21 g @ 100%; 0.5 mole), and water (79 ml) were charged to a 250 ml four-necked flask equipped with stirrer, thermometer and condenser. The temperature was raised to 90° C. over ½ hour and held between 90° and 95° C. for 10 hours. After this time, the reaction mixture was allowed to self-cool to room temperature when the pH was about 8—no adjustment was made. The solids were then filtered off, washed well with water, and pulled as dry as possible. The product was finally dried completely at 100° C. under water-pump pressure.

| Yield: | | |
|---|---|---|
| Weight of crude, dry product | = | 25.8g; 81.6% yield on anthranilic acid at 100% |
| Strength by H.P.L.C. | = | 97.0% |
| Yield of product at 100% strength | = | 79.1% on anthranilic acid at 100% |

Method II

Dry anthranilic acid (139.5 g @ 98.2%=137 g @ 100%; 1.0 mole), aqueous cyanamide liquor (135 g @ 50%=67.5 g @ 100%; 1.61 mole), and water (430 ml) were charged to a 1 liter four-necked flask fitted with stirrer, thermometer, and condenser. The temperature was raised to 90° C. over ½ hour and held between 90° and 95° C. for 10 hours. After this time, the reaction mixture was allowed to self-cool to room temperature and the pH (8.3 at this point) adjusted to 7.5 by the addition of hydrochloric acid (2.5 ml, 1:1 concentrated HCl: $H_2O$). The solids were then filtered off, washed well with water, and pulled as dry as possible. The product was finally dried completely at 100° C. under water-pump pressure.

| Yield | | |
|---|---|---|
| Weight of crude, dry product | = | 120.4g; 76.2% yield on anthranilic acid at 100% |
| Strength by H.P.L.C. | = | 91.7% |
| Yield of product at 100% strength | = | 70.2% on anthranilic acid at 100% |

The advantages of the foregoing procedures over the earlier described Stage I process of Patent Application No. 38360/76 involving hydrochloric acid acidification of the reaction mixture product are evident from a comparison of the higher strengths of product obtained. Thus a repeat of this preparation using the same materials and scale, but isolating the product by solution in acid and reprecipitating it by adding caustic soda gave 133 g of dry product (84.1% yield on anthranilic acid at 100%). The strength of this material was only 84.7%, so the yield of II at 100% strength was 71.3% on anthranilic acid at 100%.

EXAMPLE 2

The Preparation of 2-Hydrazino-quinazolin-4-one (IIIb)

Using n-butanol as Solvent

2-Amino-quinazolin-4-one (32.2 g; 0.200 mole as 100% material—actual strength 96.8%) was stirred with water (96.6 ml) to yield a paste with a total solids content of 25% w/w. To this paste in the reaction vessel was charged hydrazine hydrate (15.2 ml or 15.65 g @ 98%=15.35 g @ 100%; 0.307 mole) diluted with water (10.4 ml) to give 60% hydrazine hydrate, and n-butanol (70 ml; 56.6 g). The reaction vessel was a 250 ml four-necked flask fitted with stirrer, thermometer and a Dean and Stark head topped with a reflux condenser. The apparatus was purged with nitrogen and a nitrogen atmosphere maintained during the reaction by means of a bleed system attached to the condenser outlet and venting to atmosphere through a trap containing a known volume of standard acid (sulphuric). Ammonium chloride (2.03 g; 0.038 mole) was added quickly to the reaction mixture via the fourth neck of the flask and the mixture heated in an oil-bath to reflux over 30 minutes. Reflux was maintained while the azeotrope distilled off, the water layer being removed. During the removal of the water the temperature of the reaction mixture rose from 95° to 113° C., the bath temperature having been raised from 114° to 132° C. A total of 118.5 g of water was collected over 10 hours at reflux, after which the heating bath was removed and water (60 ml) added to the hot suspension. The mixture was allowed to cool overnight to room temperature, was then cooled in an ice-bath, and filtered. The solids were washed well with water in several portions and dried completely.

| Yield: | | |
|---|---|---|
| Weight of crude, dry product | = | 30.79g |
| Crude weight yield | = | 87.5% (on the crude 2-amino-quinazolin-4-one fed). |
| | = | 90.4% (on 2-amino-quinazolin-4-one at 100% strength) |

At the end of reaction, ammonia (0.219 mole; 109.5% theory) had been evolved, after allowing for the ammonia obtained from the ammonium chloride.

Hydrazine recovery from the filtrates yielded 6.3 g of the sulphate, equivalent to 0.049 mole hydrazine. The aqueous distillate contained 0.021 mole hydrazine and there was a further 0.001 mole in the butanol remaining in the Dean and Stark head, making a total of 0.071 mole unreacted hydrazine. Thus, the hydrazine consumption was 0.236 mole (118% of theory for formation of IIIb).

EXAMPLE 3

The Preparation of 4,5-Dihydrotetrazolo[1,5-a]quinazolin-5-one (IV)

2-Hydrazino-quinazolin-4-one (IIIb) (17.6 g; 0.1 mole), was suspended in 2 N-hydrochloric acid (78 ml; 0.156 mole) in a 600 ml beaker equipped with a thermometer and efficient stirrer. 15% w/v aqueous $NaNO_2$ solution was added at such a rate that the temperature remained between 20° and 25° C., cooling with a water bath when necessary, until a small permanent excess of nitrous acid was present. The volume of the nitrite solution used was 63 ml (=9.45 g NaNO$_2$; 0.137 mole). The reaction mixture was then stirred for 1 hour, filtered, and the solid washed acid free with water. After pulling as dry as possible on the filter, the product was dried completely in a vacuum desiccator over phosphorus pentoxide.

Yield:

| | |
|---|---|
| Weight of crude, dry product | = 16.6g; m.p. 235–236° C. |
| Crude weight yield | = 88.8% |

Using the same batch of starting material and working on the same scale, but carrying out the diazotisation at the original temperature of 8°–10° C. gave a crude weight yield of 89.5% (m.p. 235.5°–236.5° C.).

EXAMPLE 4

The Preparation of 4,5-Dihydro-4-methyltetrazolo [1,5-a]quinazolin-5-one (V)

The tetrazole (IV) (18.7 g; 0.1 mole), anhydrous sodium carbonate (22.4 g; 0.211 mole), and water (125 ml) were mixed in a 250 ml four-necked flask fitted with stirrer, thermometer, condenser, and dropping funnel containing dimethyl sulphate (18.5 ml=24.6 g; 0.195 mole). The mixture was heated to 45° C. in a water-bath and the dimethyl sulphate added dropwise over 1 hour to the stirred mixture with the temperature maintained between 40°–45° C. The reaction mixture was then stirred for a further hour at 40°–45° C., heated to 95° C. over 1 hour, allowed to self-cool to room temperature, and filtered. The solid product was washed well with water, pulled as dry as possible, and finally dried completely in a vacuum desiccator over phosphorus pentoxide.

Yield:

| | |
|---|---|
| Weight of crude, dry product | = 16.81g; m.p. 167.5° C. |
| Crude weight yield | = 83.6% |
| Strength by H.P.L.C. | = 99% |
| 100% weight yield | = 82.8% |

We claim:

1. In a process for preparing the compound 4-methyl-4,5-dihydrotetrazolo[1,5-a]quinazolin-5-one having the structural formula:

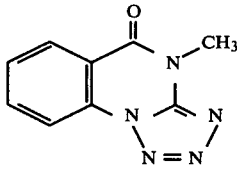

which comprises the steps of (i) bringing anthranilic acid into reaction with cyanamide at a temperature in the range of 80° to 100° C.; (ii) bringing the reaction product obtained by the foregoing step (i) into reaction with hydrazine hydrate in the presence of an organic solvent; then (iii) diazotising the hydrazino compound so formed to yield a tetrazole; and finally (iv) methylating the tetrazole, the improvement which comprises using n-butanol as the organic solvent in step (ii).

2. A process as claimed in claim 1 wherein in the first step the anthranilic acid used is essentially pure and is deployed as an aqueous paste, aqueous slurry or aqueous suspension.

3. A process according to claim 1 wherein the first step of the reaction is conducted between 90° and 95° C.

4. A process according to claim 1 wherein when the first step of the reaction has been completed the pH of the reaction mixture is adjusted to be slightly alkaline before being used in the second step of the reaction.

5. A process according to claim 1 wherein the reaction product of the first step of the reaction, namely 2-amino-quinazolin-4-one of structure:

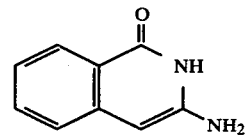

is filtered off, washed and, if desired, dried before being used in the second step of the reaction.

6. A process according to claim 1 wherein the reaction between 2-amino-quinazolin-4-one and hydrazine hydrate is carried out in n-butanol at a temperature between 90° C. and 120° C. to yield a product which is a mixture of:

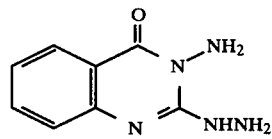

3-amino-2-hydrazino-quinazolin-4-one and

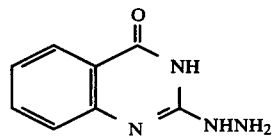

2-hydrazino-quinazolin-4-one and containing mostly the latter.

7. A process as claimed in claim 1 wherein the third, diazotisation, step is carried out by suspending the product in dilute hydrochloric acid and adding aqueous sodium nitrite slowly to the stirred suspension below about 25° C. to produce the tetrazole having the structure:

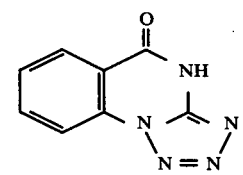

8. A process as claimed in claim 1 wherein the fourth step of the reaction comprising methylation of the tetrazole is carried out by first suspending or dissolving it in potassium or sodium carbonate solution and then bringing it into reaction with dimethyl sulphate between 40° and 45° C., or alternatively, sodium hydroxide solution is used in which case at least a part of it is added concurrently with the dimethyl sulphate; and thereafter, upon completion of the reaction warming the mixture to about 95° C. to destroy any excess of dimethyl sulphate.

9. A process as claimed in claim 1 wherein, after diazotisation, the fourth step of the reaction is carried out by adjusting the diazotisation reaction mixture to pH 9, by adding caustic soda solution or a metal carbonate to it, and then methylating with dimethyl sulphate.

* * * * *